United States Patent [19]

Smart

[11] Patent Number: 4,685,456

[45] Date of Patent: Aug. 11, 1987

[54] SELF-RETRACTING OXYGEN TUBING

[76] Inventor: Mary Smart, 404 Termino Ave., Long Beach, Calif. 90814

[21] Appl. No.: 803,320

[22] Filed: Dec. 2, 1985

[51] Int. Cl.⁴ .............................................. A62B 7/00
[52] U.S. Cl. .......................... 128/205.22; 128/204.18; 128/205.25; 128/207.18
[58] Field of Search ..................... 128/200.24, 204.18, 128/204.26, 205.17, 204.25, 205.24, 205.25, 207.18, 205.21, 205.22; 138/118

[56] References Cited

U.S. PATENT DOCUMENTS

| | | | |
|---|---|---|---|
| 2,999,497 | 9/1961 | Hamilton et al. | 128/204.18 |
| 3,021,871 | 2/1962 | Rodgers | 138/118 |
| 4,160,466 | 7/1979 | Jansson | 138/118 |
| 4,373,522 | 2/1983 | Zien | 128/200.24 |

FOREIGN PATENT DOCUMENTS 610401  6/1926  France .............................. 128/205.25

Primary Examiner—Henry J. Recla
Attorney, Agent, or Firm—Charles H. Thomas

[57] ABSTRACT

An improved, self-retracting oxygen conduit is provided for supplying oxygen to an oxygen face mask or nasal cannula on the face of a human being. One end of the improved conduit is connected to an oxygen reservoir, such as a steel cannister filled with oxygen or oxygen enriched gas and having a pressure regulator at its outlet, while the other end is connected to a facial respirator. The improved conduit is formed of a length of flexible, resilient hollow tubing, preferably formed of medical grade polyurethane. The central section of the tubing is permanently formed into a multiplicity of helical coils or loops. The coils normally reside contracted into serial contact with each other, although with the application of longitudinal tension on the tubing, the coils may be resiliently drawn apart into spatial separation from each other, thereby resiliently increasing the longitudinal distance between the opposite ends of the tubing. The tubing is not coiled at its ends. The coiled central section of the tubing thereby serves as a resilient, retraction mechanism. The overall longitudinal length of the tubing is long enough to permit the user to move his or her face relative to the oxygen reservoir. The resiliently coiled central section of the tubing prevents the tubing from developing slack lengths which may catch on doors or get caught in gurney or wheelchair wheels.

1 Claim, 6 Drawing Figures

SELF-RETRACTING OXYGEN TUBING

BACKGROUND OF THE INVENTION

1. Field Of The Invention

The present invention relates to a self-retracting oxygen conduit for coupling between an oxygen reservoir and a respirator adapted for releasable attachment to the face of a human being.

2. Description Of The Prior Art

At present, conventional hospital, convalescent home and respiratory therapy treatment involves the extensive use of oxygen and oxygen enriched gas to increase the supply of oxygen to a patient. According to present practice, oxygen is supplied to a patient through a uniform, flexible, hollow annular tubing. One end of the tubing is connected to a facial respirator, such as an oxygen face mask or nasal cannula. The other end of the tubing is connected to the outlet nozzle of the pressure regulator on a steel bottle containing oxygen or oxygen enriched gas. The tubing employed as the connecting conduit, according to present practice, is typically about ten feet in length, even though the oxygen bottle is normally carried or transported much closer to the respirator device.

The respirator inlet and the oxygen reservoir outlet are normally separated by a distance of no more than about two feet. The additional length of oxygen conduit is necessary to accomodate changes in the position of the user wearing the respirator, movement of the user's head, relocation of the oxygen reservoir, and other relative movement between the user wearing the respirator and the oxygen reservoir. Failure to provide a sufficient length of oxygen conduit can result in inadvertant decoupling of the conduit from either the respirator or the oxygen reservoir, or difficulty in manipulating and moving the oxygen reservoir and the user together. Critical time can be lost if manipulation of the position of the user and the oxygen reservoir is hindered by the fact that the oxygen conduit is too short. When treating a patient in an emergency situation any loss of time can result in death or serious injury to the patient. Consequently, a generous length of connecting conduit is supplied for connection between a facial respirator and an oxygen reservoir in the environment of hospital emergency rooms, hospital convalescent rooms, respiratory therapy centers, and the like.

Because a considerable length of conduit tubing is provided between a facial respirator and an oxygen reservoir in order to maintain a supply of oxygen while a patient moves, or is moved about, long loops of slack tubing are typically present when the oxygen reservoir is at its normal proximity relative to the patient or other user. In many instances the user carries the oxygen bottle in a pouch suspended from a strap worn over the user's shoulder. In other instances the oxygen bottle is carried in the same type of pouch suspended from a strap slung over the back of a wheelchair or carried on a hospital cart or gurney. Usually, the oxygen reservoir is seldom separated from the facial respirator by a distance of greater than two feet. With a conventional ten foot length of oxygen tubing there is therefore a great deal of slack in the conduit connecting the oxygen reservoir to the facial respirator.

The existence of slack lengths of oxygen tubing has presented considerable problems. The slack loops of tubing frequently become entangled in the wheels and axles of hospital carts and wheelchairs. Also, the slack loops are frequently caught in clothing and doors and not infrequently become hooked about the arms and handles of wheelchairs and other devices employed in hospitals, convalescent homes, and locations where respiratory therapy is conducted. The snagging of oxygen tubing while a patient and an oxygen reservoir are moved is at least inconvenient and upsetting to the patient, and can be quite dangerous. An oxygen mask can be abruptly yanked from the face of the patient when the connecting conduit is suddenly snagged. Also, critical time in the treatment of a patient can be lost in freeing a fouled oxygen conduit.

SUMMARY OF THE INVENTION

According to the present invention, the necessary length of oxygen tubing is provided between a facial respirator and an oxygen reservoir, but the central portion of the conduit is formed into permanent, resilient, circular coils or loops. The overall linear distance of separation of the ends of the improved conduit, with the coil loops retracted, is about three feet. Preferably, there is an uncoiled or straight length of about twelve inches at one end of the conduit which is coupled to the inhalation port of a conventional facial respirator, such as an oxygen mask or nasal cannula. At the opposite end of the tubing there is preferably a straight or uncoiled length of approximately eighteen inches. This uncoiled length facilitates connection of this other end of the tubing to the outlet nipple or fitting of a conventional pressure regulating valve on an oxygen bottle.

When the improved oxygen conduit is employed by a user wearing a facial respirator and carrying an oxygen bottle by means of a pouch on a shoulder strap, the twelve inch length of uncoiled tubing extends downwardly from the facial respirator to about the chest area of the user. The coiled section of the tubing prevents the formation of slack loops in the tubing, and hangs comfortably against the torso in the chest area of the patient so as not to interfere with normal sideways movement of the user's head. The longer, eighteen inch length of uncoiled tubing may be easily connected to the outlet port of the pressure regulator of the oxygen reservoir, and creates a sufficient distance of separation between the coiled section and the oxygen reservoir so that the coils of the conduit do not become tangled in the pressure regulating mechanism of the oxygen reservoir.

Because the central section of the improved conduit of the invention is coiled, it can be stretched to nearly its full length when necessary, without disturbing the connections to either the oxygen supply or the oxygen inhalation mask or cannula. Longitudinal tension on the conduit allows the coils to separate from each other with a spring-like action to allow the user to move some distance or be moved relative to the oxygen reservoir without stretching the tubing and without exerting any significant force on the couplings to the facial respirator and the oxygen reservoir. As the facial respirator and the oxygen reservoir are returned to their normal proximity, the permanent coils of the conduit contract toward each other, thus automatically taking up slack which would otherwise develop in the oxygen conduit. The improved oxygen conduit of the invention allows the conduit to be fully extended, when necessary, yet prevents the formation of slack loops in the absence of tension on the conduit.

The principal area of application envisioned for the improved oxygen conduit of the invention is for use with patients in hospitals and in respiratory therapy centers, and for use by patients convalescing at homes or in convalescent centers. However, the invention also has applicability to other environments in which oxygen masks are employed. For example, the invention may also be employed in commercial passenger aircraft. Should cabin pressure in such an aircraft drop, oxygen masks are automatically dropped from compartments near the passengers. If the oxygen masks are coupled to the oxygen supply by means of the conduits of the invention, the oxygen masks are conveniently at hand and are held by the conduits in such a fashion that the conduits of adjacent masks are unlikely to become entangled with each other. Nevertheless, the masks can be drawn by the passengers and extended a considerable distance for placement on the faces of the passengers.

In one broad aspect the present invention may be considered to be a self-retracting oxygen conduit for coupling between an oxygen reservoir and a facial respirator adapted for releasable attachment to the face of a human being. The oxygen conduit of the invention is comprised of the length of flexible, resilient hollow tubing having opposite ends and a central section permanently formed into a multiplicity of helical coils which normally reside contracted into serial contact with each other. The helical coils may be resiliently drawn apart into spatial separation from each other, thereby resiliently increasing the longitudinal distance between the opposite ends of the tubing.

In another broad aspect the invention may be considered to be an improvement in a connecting conduit formed of hollow flexible tubing for supplying oxygen to a human being from a reservoir to a facial attachment in which the conduit has opposite ends connected to the reservoir and to the facial attachment. The improvement, according to the invention, is comprised of a multiplicity of helical coils defined in the tubing between the opposite ends thereof. The coils are permanently formed in the tubing to resiliently contract together into serial contact with each other in the absence of longitudinal tension on the tubing. The tubing is resiliently extendable so that longitudinal tension on the tubing increases the distance of separation between the opposite ends thereof without stretching the tubing. This is accomplished by drawing the coils apart to define spatial separations between adjacent coils. Upon release of longitudinal tension on the tubing, the coils contract toward each other, thereby preventing the tubing from slackening.

In still another broad aspect the invention may be considered to be a method of maintaining a supply of oxygen to a human being through a facial respirator from an oxygen reservoir while the human being and the oxygen reservoir are both in motion. According to the method of the invention, the respirator is coupled to the oxygen reservoir through a conduit constructed of a length of flexible, resilient hollow tubing having opposite ends and a central section permanently formed into a multiplicity of helical coils. The helical coils are resiliently contracted together in serial contact with each other, and may be resiliently drawn apart into spatial separation from each other. The conduit therefore accomodates changes in distance between the opposite ends of the tubing. The coils prevent the tubing from slackening.

The invention may be described with greater clarity and particularity by reference to the accompanying drawings.

DESCRIPTION OF THE EMBODIMENT AND IMPLEMENTATION OF THE METHOD

Figure 1:
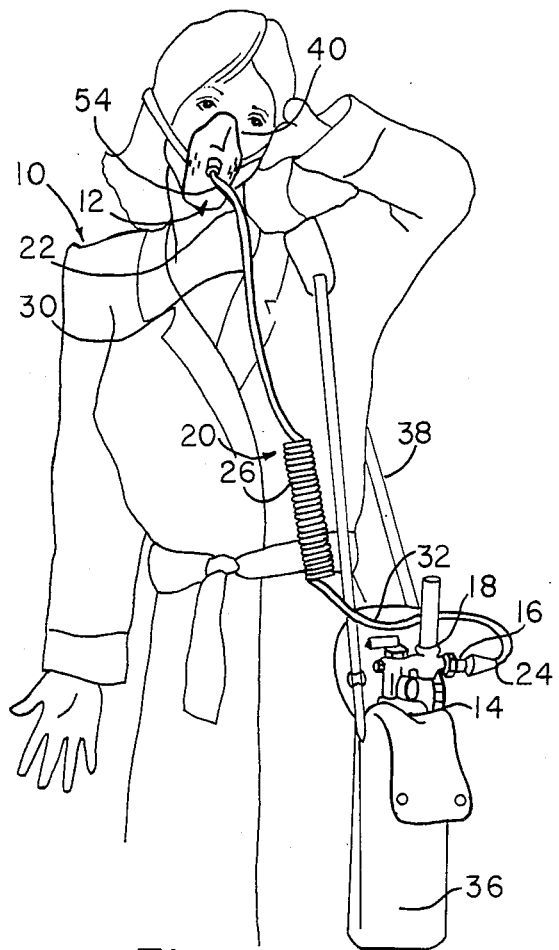
FIG. 1 illustrates use of a preferred embodiment and practice of the method of the invention.

FIG. 1 illustrates an individual human being, indicated at 10, wearing a facial respirator attachment in the form of an oxygen mask 12 which receives oxygen supplied by an oxygen reservoir 14. The oxygen reservoir 14 is a conventional, steel cannister, filled with pressurized oxygen and has a pressure regulating valve 18 with an outlet port 16. The oxygen reservoir 14 is connected to the face mask 12 by means of an improved, self-retracting oxygen conduit 20 constructed according to the present invention.

Figure 2:
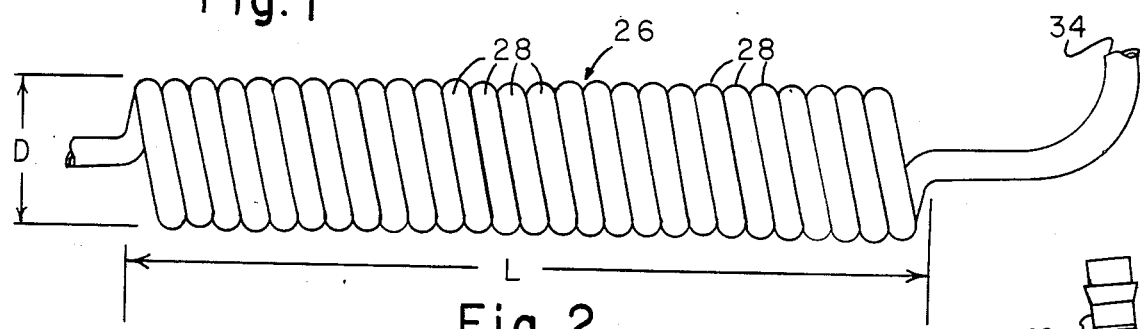
FIG. 2 is a detail of the central coiled section of the embodiment of the conduit employed in FIG. 1 in a while contracted state.
Figure 3:
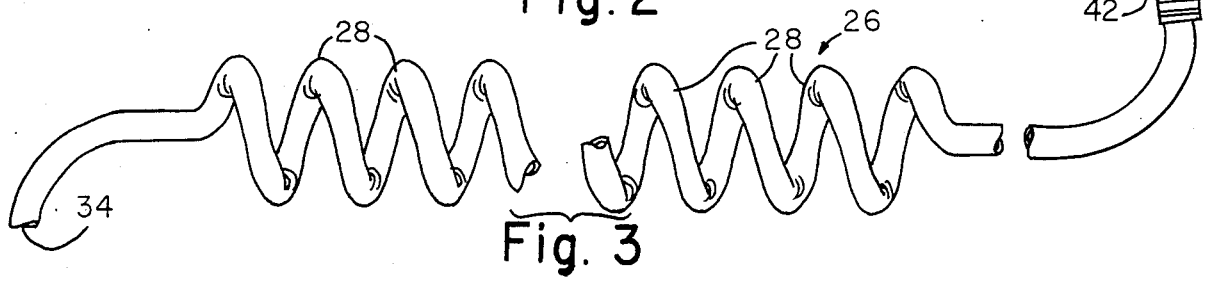
FIG. 3 is a detail of the central coiled section of the embodiment of the invention employed in FIG. 1 while in an extended state.

The oxygen conduit 20 is formed of hollow annular, medical grade polyurethane tubing and has first and second opposite ends 22 and 24 and a central section 26. As illustrated in FIG. 2, the central section 26 has a multiplicity of helical coils 28 permanently formed or defined in the tubing forming the conduit 20. The coils 28 resiliently contract together into serial contact with each other in the absence of longitudinal tension on the conduit tubing, as depicted in FIG. 2. The conduit tubing is resiliently extendable so that longitudinal tension thereon increases the longitudinal distance between the opposite ends 22 and 24 of the conduit 20 without stretching the tubing. This is accomplished by exerting longitudinal tension on the central section 26 of the conduit 20 to draw the coils 28 apart to define spatial separations between adjacent coils, as depicted in FIG. 3. Upon release of longtudinal tension on the conduit tubing, the coils 28 contract toward each other to prevent the tubing from slackening, as illustrated in FIG. 2.

In the preferred embodiment of the invention depicted in FIG. 1, the tubing of the conduit 20 is coiled at 26 between a first, uncoiled section 30 about twelve inches in length at the first end 22, and a second uncoiled section 32, about eighteen inches in length at the other end 24. The overall length of the conduit 20, as measured longitudinally along the axis of the lumen 34 therethrough, is about ten feet. Preferably, the inner diameter of the conduit tubing, and hence the diameter of the lumen 34, is about one-eighth of an inch. The tubing preferably has an outer diameter of about 0.235 inches. The coils 28 are about one and three-eighths inches in diameter, as measured perpendicular to the axis of the coiled section 26. This diameter is indicated at D in FIG. 2. As is evident, a significant portion of the overall length of the tubing of the conduit 20 is included in the spirally formed central section 26. When the coils 28 are contracted, as depicted in FIG. 2, the overall length of the central section 26, as measured along the axis of the coils 28, is about six inches. This distance is indicated at L in FIG. 2. Thus, the distance between the opposite ends 22 and 24 of the conduit 20 is preferably about three feet, in the absence of longitudinal tension on the central coiled section 26.

As illustrated in FIG. 1, the oxygen reservoir 14 may be carried in a pocket-like pouch or pack 36 suspended from a shoulder strap 38 carried on the shoulder of the user 10. With the oxygen mask 12 positioned on the face 40 of the user as illustrated, there is no longitudinal tension on the conduit 20. The first end 22 is connected to the facial oxygen mask 12, and the twelve inch length of the section 30 allows the bulk of the coiled section 26 to hang comfortably in the chest area against the torso of the user 10, a short distance from the user's face 40. The eighteen inch length of the uncoiled section 32 at the opposite end 24 of the conduit 20 may be conveniently connected to the leuer fitting 16 at the outlet of the pressure regulator 18 of the oxygen reservoir 14.

As is evident from FIG. 1, the coiled section 26 prevents slack loops of the type which occur in conventional oxygen conduits from forming in the improved conduit 20. In conventional conduits such slack loops frequently become snagged or catch on doors and on the wheels and axles of wheelchairs and hospital carts. Nevertheless, the conduit 20 can be extended to its full ten foot length by the application of longitudinal tension on the opposite ends of the coiled section 26. Such longitudinal tension does not cause tugging upon the ends 22 and 24, however. To the contrary, the application of such tensile force merely separates the coils 28 in the manner depicted in FIG. 3 to accomodate relative movement between the face 40 of the user 10 and the oxygen reservoir 14.

Preferably, the conduit 20 is constructed of medical grade polyurethane tubing. Polyurethane has better memory characteristics than the conventional medical grade vinyl tubing and is better able to permanently maintain the contracted helical configuration of the coils 28. The tubing is first produced by a conventional extrusion process, and the central section 26 is then helically wound by hand on a mandrel. The central section 26 is then heated to plastically deform the tubing in the central section 26. After cooling, the tubing is removed from the mandrel. Coiled, medical grade polyurethane tubing of his type may be obtained from the Freelin-Wade Company of McMinnville, Oreg.

Figure 5:
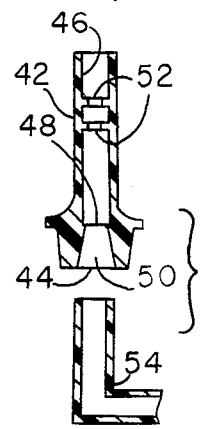
FIG. 5 is a sectional detail illustrating connection of an end fitting of a preferred embodiment of the invention to one type of connector.
Figure 6:
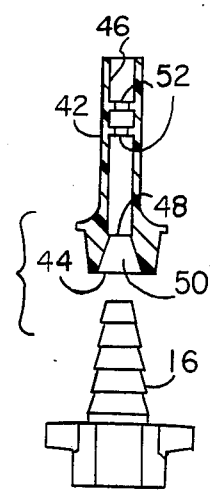
FIG. 6 is a sectional detail illustrating connection of an end fitting of a preferred embodiment of the invention to a different type of connector.

Preferably the ends 22 and 24 of the tubing forming the conduit 20 are provided with identical end fittings, one of which is indicated at 42 in FIG. 3. As illustrated in FIGS. 5 and 6, each of the end fittings 42 defines a circular mouth 44, an interior cylindrical socket 46 for receiving a tubing end, and a throat 48 which is narrower than both the mouth 44 and the socket 46. The throat 48 is located between the mouth 44 and the socket 46. A frusto conical radially inwarding facing surface 50 converges from the mouth 44 toward the throat 48. The socket 46 has a cylindrical inner surface with a pair of radially inwardly raised circular ribs 52 defined thereon. The diameter of the socket 46 is large enough to receive an end of the conduit tubing without inordinately resisting insertion of the tubing. The resilient annular ribs 52 firmly grip the end of the tubing therewithin as it is inserted into the socket 46 to form a gas tight seal between an end of the tubing and the socket 46.

The frusto conical surface 50 is adapted to readily receive a cylindrical annular coupling 54 of the type with which an oxygen mask 12 is typically provided. As the tip of the coupling 54 is inserted into the mouth 44 of the fitting 42 the surface 50 directs the tip of the coupling 54 toward the fitting throat 48. The structure of the fitting 42 is sufficiently flexible so that the throat 48 resiliently yields to admit and firmly grip the outer surface of the coupling 54. The grip of the throat 48 on the coupling 54 ensures a gas tight seal therewith.

Figure 4:
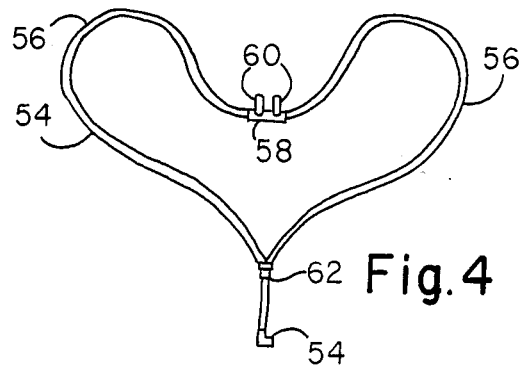
FIG. 4 illustrates a typical nasal cannula to which the conduit of the invention may be connected.

The improved self-retracting oxygen conduit 20 may also be employed with a different type of facial respirator, such as a typical nasal cannula, depicted at 54 in FIG. 4, instead of a face mask 12. The nasal cannula 54 has a pair of loops 56 which are typically hooked over the ears of a patient. An outlet fitting 58 is located between the loops 56 and includes a short pair of parallel, radially directed ducts 60, which extend into the nostrils of a wearer. The opposite ends of the loops 56 converge in a junction fitting 62 which is connected by a short length of tubing to the same type of coupling 54, depicted in FIG. 5. A nasal cannula 54 can be worn more comfortably by a wearer than an oxygen face mask 12, and is typically used where a patient requires only supplementary oxygen, rather than pure oxygen.

The conduit 20 also includes an identical fitting 42 at its opposite end 24. While either fitting 42 can readily receive the tip of a cylindrical annular coupling 54, they are configured to likewise receive the terraced nipple of a conventional leuer fitting 16, depicted in FIG. 6. The pressure regulators 18 which are connected to the ports of conventional oxygen bottles typically include outlets in the form of leuer fittings 16. Thus, the end fittings 42 of the conduit 20 are readily adaptable to receive different types of couplings, such as the couplings 54 and 16 which are commonly used in the field of respiratory therapy.

As illustrated in FIG. 1, the improved, self-retracting conduit 20 is uniquely adapted to maintain a supply of oxygen to a human being through a facial respirator from an oxygen reservoir even though the user and the oxygen reservoir are both in motion. The resiliently contractable coils 28 allow normal, side to side head movement of the user 10, and will separate apart to accomodate lowering of the oxygen reservoir pack 36 and removal of the shoulder strap 38 from the shoulder of the user. When the oxygen reservoir 14 is moved away from the face mask 12, there is no tugging or pulling on the coupling 54 thereto, since the coils 28 readily spread apart and separate from each other in the manner depicted in FIG. 3. The improved, self-retracting conduit 20 thereby accomodates changes in distance between the opposite ends 22 and 24 of the conduit tubing. Conversely, the coils 28 prevent the tubing from slackening when the oxygen reservoir 14 is carried in its normal position on the shoulder strap 38. The improved conduit 20 thus prevents the formation of slack loops which could otherwise become caught and snagged during movement of the user 10.

Undoubtedly, numerous variations and modifications of the invention will become readily apparent to those familiar with supplying oxygen to human beings through facial respirators. For example, while the preferred length of the coiled section 26 of the improved conduit 20 is about six inches, the most desireable length may vary, depending upon the height of the individual involved. The central section 26 is preferably between about six and about seven and one half inches in length L in the absence of longitudinal tension on the conduit tubing. However, the most appropriate length may vary, depending upon whether the conduit 20 is to be used connected to an oxygen reservoir worn on a shoulder strap, carried on the back of a wheelchair, or carried on a hospital cart or gurney.

Accordingly, the scope of the invention should not be construed as limited to the specific embodiment depicted and manner of implementation of the manner of the method described. Rather, the scope of the invention is defined in the claims appended hereto.

I claim:

1. A method of maintaining a supply of oxygen to a patient through a facial respirator from an oxygen reservoir while said patient and said oxygen reservoir are both in motion and are moveable relative to each other comprising: coupling said respirator to said oxygen reservoir through a conduit constructed of a length of flexible, resilient hollow medical grade tubing having opposite ends and a central section permanently formed into a multiplicity of helical coils which are resiliently contracted together in serial contact with each other in the absence of longitudinal tension on said opposite ends, applying longitudinal tension upon said opposite ends of said conduit by moving said respirator and said oxygen reservoir apart relative to each other to thereby resiliently draw said coils apart into spatial separation from each other without stretching said tubing and without exerting tension on said reservoir and said respirator, and releasing said tension by moving said respirator and said oxygen reservoir toward each other to allow said coils to contract with sufficient spring action to return to serial contact with each other when said longitudinal tension is removed, whereby said conduit accommodates changes in distance between said opposite ends of said tubing and said coils prevent said tubing from slackening when longitudinal tension on said ends is released, and further employing tubing having about a twelve inch uncoiled section at one of said ends and about an eighteen inch uncoiled section at the opposite of said ends and further comprising connecting said section about twelve inches in length to said respirator and said section about eighteen inches in length to said oxygen reservoir, whereby when the improved oxygen conduit is employed by a user wearing the facial respirator and carrying the oxygen reservoir at approximately waist height, the twelve in length of tubing extends downwardly from the facial respirator to about the chest area of the user and the coiled section prevents the formation of slack loops in the tubing while hanging comfortably against the torso in the chest area of the user so as not to interfere with normal sideways movement of the user's head.

* * * * *